(12) United States Patent
Ashcraft et al.

(10) Patent No.: US 6,810,337 B1
(45) Date of Patent: Oct. 26, 2004

(54) SYSTEMS AND METHODS FOR TRACKING THE AGE OF AIR PRESSURE AND FLOW ALARM CONDITIONS WITHIN A PRESSURIZED CABLE NETWORK

(75) Inventors: Philip B. Ashcraft, Cumming, GA (US); Ronnie L. Rozier, Lithonia, GA (US); Max L. Waldrop, Jr., Aiken, SC (US)

(73) Assignee: BellSouth Intellectual Property Corporation, Wilmington, DE (US)

( * ) Notice: Subject to any disclaimer, the term of this patent is extended or adjusted under 35 U.S.C. 154(b) by 134 days.

(21) Appl. No.: 10/093,196

(22) Filed: Mar. 7, 2002

(51) Int. Cl.[7] .......................... G01F 23/00; G01N 11/00
(52) U.S. Cl. .......................................................... 702/51
(58) Field of Search ............................ 702/51, 50, 47, 702/184, 185, 188, 79, 89, 125, 176, 187; 340/604, 605, 611, 614

(56) References Cited

U.S. PATENT DOCUMENTS

| | | | | |
|---|---|---|---|---|
| 5,708,364 A | * | 1/1998 | Vokey et al. | 324/523 |
| 5,883,815 A | * | 3/1999 | Drakulich et al. | 364/509 |
| 6,018,300 A | * | 1/2000 | Dowden et al. | 340/635 |
| 6,600,423 B1 | * | 7/2003 | Rozier et al. | 340/611 |
| 6,714,884 B2 | * | 3/2004 | Dor et al. | 702/82 |
| 6,737,976 B2 | * | 5/2004 | Rozier et al. | 340/611 |
| 6,754,595 B1 | * | 6/2004 | Rozier et al. | 702/50 |
| 2003/0102966 A1 | * | 6/2003 | Konchin et al. | 340/445 |

OTHER PUBLICATIONS

U.S. patent application Ser. No. 09/968,300, entitled "Index Ranking Systems and Methods For Monitoring Air Pressure and Flow", Filed Oct. 1, 2001—Inventors—Aschraft et al.
U.S. patent application entitled "Systems and Methods for Remotely Controlling A Cable Pressure Monitoring Unit", filed Oct. 8, 2001—inventors—Rozier et al.
U.S. patent application entitled "Systems and Methods For Bypassing The Flow of Fluid Around Flow Finding Devices", filed Oct. 16, 2001—Inventors—Rozier et al.
U.S. patent application entitled "Pressure Alarms and Report System Module For Proactive Maintenance Application", filed Nov. 30, 2000—Inventors—Beamon et al.
U.S. patent application Ser. No. 09/978,320, Rozier et al.
U.S. patent application Ser. No. 09/978,320, Beamon et al.

* cited by examiner

*Primary Examiner*—Michael Nghiem
(74) *Attorney, Agent, or Firm*—Kirkpatrick & Lockhart LLP

(57) ABSTRACT

Systems and methods for monitoring pressurization performance of a cable network that may include detecting alarm conditions within the cable network, recording the time and date during which each alarm condition was initially detected, and calculating a length of time for each detected alarm condition during which the detected alarm condition remains unremediated.

46 Claims, 4 Drawing Sheets

| Wire Center | Line | Input | Unit | Mod | Dev# | CO Panel Alarms Min PSI 9.5/Max PSI 11 | Read | Dev Type | CL | Date | Time | Alm-Date | Alm-Age |
|---|---|---|---|---|---|---|---|---|---|---|---|---|---|
| albygama | 2 | 20 | 8 | Ded | 283 | CO Air Pipe Pres TD RT 7 Pipe C N/3 0 | 8.49 | Pres Off | SP | 11/13 | 02:50 | 09/18/2001 | 56 |
| amrcgama | 2 | 32 | 2 | Ded | 15 | CO Air Pipe B Route 2 PTD HC/11 0 | 8.96 | Pres Off | SP | 11/13 | 02:27 | 11/10/2001 | 3 |
| albygama | 4 | 73 | 1 | Ded | 4 | CO Dist Pres TD RT 1 0 | 9.47 | Pres Off | DP | 11/13 | 02:47 | 11/03/2001 | 10 |
| albygama | 6 | 26 | 2 | Ded | 27 | CO Dist Pres TD RT 1 0 | 9.47 | Pres Off | DP | 11/13 | 02:47 | 11/07/2001 | 6 |
| albygama | 2 | 19 | 4 | Ded | 139 | CO Air Pipe Pres TD RT 4 Pipe A N/1 0 | 9.47 | Pres Off | SP | 11/13 | 02:49 | 09/18/2001 | 56 |
| albygama | 2 | 60 | 7 | Ded | 214 | CO Air Pipe Pres TD RT 6 Pipe B 0 | 9.48 | Pres Off | SP | 11/13 | 02:50 | 09/18/2001 | 56 |
| Wire Center | Line | Input | Unit | Mod | Dev# | End of Air pipe Alarms -- Min PSI | Read | Type | CL | Date | Time | Alm-Date | Alm-Age |
| albygama | 61 | 31 | 2 | Sub | 85 | PP F Cordele/PNEBLUF 39/926 MH CR17 32 | 5.71 | Pres | EP | 11/13 | 02:48 | 09/18/2001 | 56 |
| Wire Center | Line | Input | Unit | Mod | Dev# | Air Pipe Alarms Min PSI 7. | Read | Type | CL | Date | Time | Alm-Date | Alm-Age |
| albygama | 35 | 73 | 2 | Sub | 57 | PP F 1529 E.Broad 21/906 MH A23 16 | 0.09 | Pres | PP | 11/13 | 02:48 | 09/18/2001 | 56 |
| albygama | 58 | 30 | 2 | Sub | 82 | PP F Cordele/Clark 39/902 MH CR7 30 | 2.61 | Pres | PP | 11/13 | 02:48 | 09/18/2001 | 56 |

FIG. 3

SYSTEMS AND METHODS FOR TRACKING THE AGE OF AIR PRESSURE AND FLOW ALARM CONDITIONS WITHIN A PRESSURIZED CABLE NETWORK

BACKGROUND OF THE INVENTION

Field of the Invention

The subject invention relates generally to systems and methods for monitoring fluid pressure and fluid flow within pressurized cable networks and, more particularly, to systems for monitoring and tracking the age of air pressure and/or air flow alarm conditions detected by monitoring systems that monitor the air pressure and air flow within pressurized telecommunication cable networks.

DESCRIPTION OF THE INVENTION BACKGROUND

The cables that make up a telecommunications network typically include a sheath made of a water-resistant or waterproof material, such as lead or polyethylene. These sheaths typically encompass wires, such as copper wires, and an insulation material that separates individual conductor pairs. This insulation material may be, for example, paper, pump, or plastic.

Exposure of the interior of a cable to water or moisture may lead to a number of problems. For example, exposure of the interior of a cable to moisture may destroy the insulating characteristics of the paper or pump. If cracks develop in the sheath of a cable or the sheath of a cable is sliced, water may enter the cable and electrolysis may occur, resulting in faulted conductor pairs.

Each year, telecommunication companies spend large amounts of money pumping low-humidity air into their cables and pipes that carry and enable the transmission of voice and data information. This low-humidity air creates positive pressure within the cable sheaths, enabling them to resist standing water, moisture damage, and the like. Such standing water and moisture damage may lead to noise on the line, data transmission errors, and, ultimately, complete cable failure. Thus, the basic premise of cable pressurization is to keep the pressure within a cable in excess of the pressure that could be applied by standing water. To this end, telecommunications companies and related industry associations have established minimum air pressure standards for underground, direct-buried, and aerial cables. For example, a minimum air pressure of six (6) pounds per square inch (PSI) may be required for underground cables, a minimum air pressure of three (3) PSI may be required for direct-buried cables, and a minimum air pressure of one (1) PSI may be required for aerial cables, as they are less at risk from water damage.

The air pumped into pressurized telecommunications cables originates from a plurality of air compressors, typically located in a company's "central offices" or other facilities. These air compressors are preferably coupled with dryers or dehumidifiers operable for removing residual moisture from the air. Because a pressurized cable route may include a plurality of discrete sections of cable, each potentially thousands of feet long, the air pressure tends to decrease as the distance from a central office, and a given air compressor, increases. This pressure drop is due, in part, to the presence of inevitable leaks. Therefore, air pressure is typically reestablished along a cable route by running an air pipe along the route and introducing air at a plurality of fixed points. The air pipe is connected to a plurality of manifolds that distribute air to the cables at, for example, each utility bole, making these connections easier to maintain.

In order to maintain a pressurized cable route, a plurality of air pressure and flow monitoring devices or sensors are placed at strategic points along the route (for example, at each manifold). These sensors are typically standard pressure transducers. The air pressure sensors measure the amount of air compression in a given cable volume at a given time in PSI. The flow sensors measure the standard cubic feet of air to pass through a given cable volume in a given period of time in standard cubic feet per hour (SCFH) or standard cubic feet per day (SCFD). Both the air pressure sensors and the flow sensors are linked to monitors in the various central offices so that readings may be taken by maintenance technicians at predetermined times. If the air pressure or flow level for a given sensor drops below a predetermined value, an alarm is tripped. A maintenance technician may then be dispatched to repair the affected cable, air pipe, manifold, etc.

Those who manage the pressurized cable route may collect data from the various central offices and, using existing software programs, analyze maintenance expenditures, track maintenance technician efficiency, identify problems, and rate overall pressurization system quality. This is typically done hierarchically, e.g., by region, district, office, area, and the like. These software programs, such as that used by GTE (the "GTE Air Pressure Status Report"), typically generate summary information related to such items as the number of air pressure and flow alarms for a given period of time, the number of maintenance technician dispatches for a given period of time, a pressurization system quality index (SQI), the total man-hours for a given period of time or per sheath-mile, the operation of given air compressors or dryers, and problem regions, districts, offices, areas, etc. Although marginally useful, this information is typically complex, often inaccurate, and generally expensive to collect. More importantly, this information is dependent upon the schematics of a given pressurized telecommunications cable route, and must take the network layout into account.

Also, many of the reports generated by such systems fail to indicate when an alarm has occurred and how long the alarm condition has been in existence without being remediated. Thus, although the report may indicate that an alarm has occurred, the manager responsible for maintaining the system does not know when it occurred and, perhaps more importantly, is unable to ascertain how long the alarm condition has existed without being rectified. Without such information, a manager is unable to prioritize repair activities in the order of alarm occurrence. Thus, there is a need for systems and methods that provide inexpensive and accurate information related to the age of pressure and/or flow alarm conditions occurring in pressurized cable networks.

SUMMARY OF THE INVENTION

In accordance with one embodiment of the present invention, there is provided a method of monitoring pressurization performance of a cable network that may include detecting alarm conditions within the cable network, recording the time and date during which each alarm condition was initially detected, and calculating a length of time for each detected alarm condition during which the detected alarm condition remains unremediated.

Accordingly, the various embodiments of the present invention provide management with tools for monitoring the remediation progress and prioritization of alarm conditions occurring within networks of pressurized cables. Those of ordinary skill in the art will readily appreciate, however, that these and other details, features and advantages will become further apparent as the following detailed description of the embodiments proceeds.

BRIEF DESCRIPTION OF THE DRAWINGS

FIG. 3 is an example of a report generated using the systems and methods of the present invention.

DETAILED DESCRIPTION OF THE EMBODIMENTS OF THE INVENTION

Figure 1:
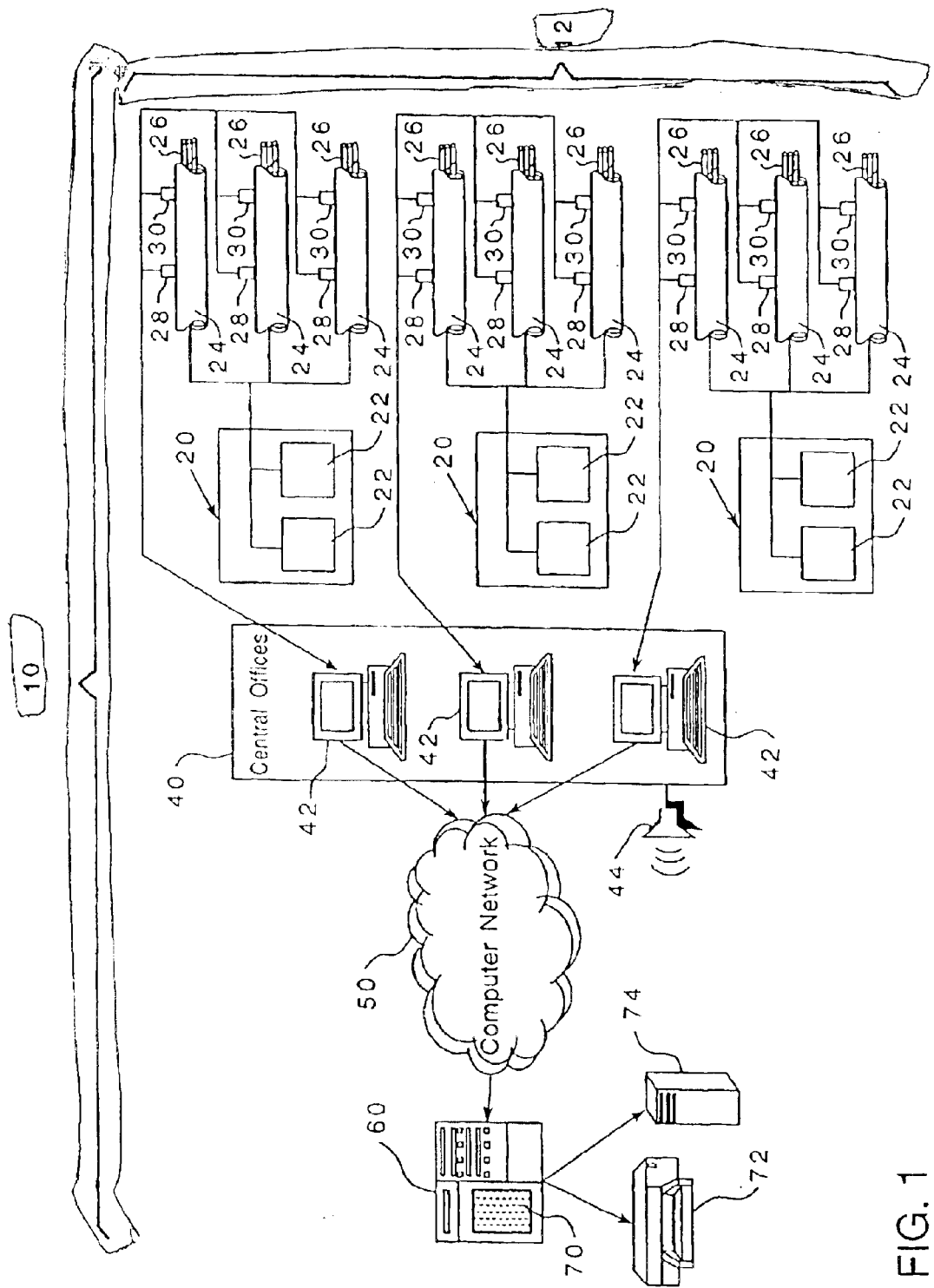
FIG. 1 is a schematic diagram of one embodiment of a system for monitoring the pressurization performance of a cable network.

Referring now to the drawings for the purposes of illustrating the present embodiments of the invention only and not for the purposes of limiting the same, it is to be understood that standard components or features that are within the purview of an artisan of ordinary skill and do not contribute to the understanding of the various embodiments of the invention are omitted from the drawings to enhance clarity. One embodiment of the present invention is directed to a system 10 for monitoring the fluid pressure and/or fluid flow within a pressurized cable network 12 which includes a plurality of pressure monitoring or flow monitoring devices or sensors. Although various embodiments of the present invention are particularly well-suited for use in connection with a system for monitoring the air pressure and air flow within a pressurized telecommunications cable network, those of ordinary skill in the art will readily appreciate that the systems and methods of the present invention may be effectively employed with a myriad of other pressurized cable arrangements. Furthermore, as used herein, the term "fluid" may mean air, any liquid, gas, or semisolid gel.

More particularly and with reference to FIG. 1, in one embodiment, the system 10 may include a plurality of wire centers 20 that may contain, among other things, a plurality of conventional compressor/dehydrator machines 22 that are operably coupled to series of conduits 24 that support bundles of cables 26, such a fiber optic cables therein. Located in the conduits 24 at strategic locations may be a plurality of pressure sensors 28 and/or flow sensors 30 that indicate the flow and pressure, respectfully, of the compressed fluid such as air supplied by the compressor/dehydrators 22. These sensors may be, for example, standard pressure transducers that utilize variations in electrical resistance to detect fluid pressure conditions, flow conditions, and the like. The pressure sensors 28 may measure the amount of fluid compression in a given cable volume at a given time typically in pounds per square inch (PSI). The flow sensors 30 may measure the standard cubic feet per hour (SCFH) or standard cubic feet per day (SCFD).

The system 10 may further include a plurality of central offices 40 that each service a particular geographical area. Each central office 40 may have a monitoring unit 42 that communicates with the various wire centers that are associated with that particular central office 40. These monitoring units 42 may be, for example, computers, electronic panels, mechanical panels, etc that communicate with the sensors (28, 30) of corresponding wire centers 20. Such flow transducer sensors, pressure transducer sensors and the pressure and flow monitoring units are commercially available from Sparton Technology, Inc. of 2400 East Ganson Street, Jackson, MI 49202 under, for example, Model No. 535300B. However, other systems/components could conceivably be employed.

The pressure sensors 28 and the flow sensors 30, in conjunction with the monitoring units 42, monitor the pressure and flow of the compressed fluid, usually air, within the respective conduits 24 to prevent moisture, debris, etc. from infiltrating into the conduit 24. Thus, a decrease in pressure or an increase in flow rate could mean that the conduit 24 in which it is mounted has ruptured or has otherwise developed a leak. Thus, for example, if the fluid pressure detected by a given pressure sensor 28 is below a predetermined value (i.e., 9.5 psi or other predetermined minimum values) or is above a predetermined value (i.e., 11 psi or other predetermined maximum values) an alarm 44 may be tripped in the respective central office 40. A maintenance technician may then be dispatched to remediate the affected conduit. Thus, the monitoring units 42 provide automated surveillance of output signals from the pressure sensors 28 and the flow sensors 30. An alarm condition is "remediated" when the condition that has caused the detected pressure and/or flow rate to fall outside of an acceptable range or below an accepted minimum level or above an accepted maximum level has been corrected such that the pressure and/or flow rate for that particular section of the cable network again falls within acceptable levels. Upon correction of the leak or other condition that resulted in the tripping of the alarm 44, the technician may reset the alarm 44. As will be discussed below, the technician or other personnel may also enter information in the computer network indicating that the alarm condition has been remedied.

As described above, management collects data from the various central offices 40 concerning the alarm conditions and their respective locations and uses the data to analyze maintenance expenditures, track maintenance technician efficiency, identify problems, and rate overall pressure system quality. This is typically done hierarchically, e.g., by region, district, office, area, and the like. The software programs used typically generate summary information related to such items as the number of air pressure and flow alarms for a given period of time, the number of maintenance technicians dispatched for a given period of time, a pressurization system quality index, the total man-hours for a given period of time or per sheath-mile, the operation of given air compressors or driers and problem regions, districts, offices, areas, etc.

Typically, pressurization-related data are communicated from the various central offices 40 to management via shared computer files, the telephone, facsimile, etc. In one embodiment, the system 10 includes a computer network 50 operable for communicating pressurization-related data from the various central offices 40 to a server 60. The computer network 50 may be, for example, a local area network (LAN), a wide-area network (WAN), or a globally-distributed computer network, such as the Internet. The server 60 may be, for example, a file server, a web server or a database server. The server 60 may include a processor and a memory. The processor may be a microprocessor, such as that manufactured by Advanced Micro Devices, Inc. (Sunnyvale, Calif.), Intel Corporation (Santa Clara, Calif.), Motorola, Inc. (Schamburg, Ill.), International Business Machines Corp (Armonk, N.Y.), and Transmeta Corp (Santa Calar, Calif.). The server may be, for example, a Compaq ProLiant ML530 server (Compaq Corporation, Houston, Tex.). The memory may include random-access memory (RAM) and a read-only memory (ROM), as well as other types of memory.

An alarm age module 70 may be disposed within the server 60. The alarm age module 70 may comprise an application or algorithm, operable for generating summary information relating to the age of an alarm condition (i.e., the time in minutes, hours, days, months, years, etc. that an alarm condition remains unrepaired from its time of initial occurrence) and, if desired, other information that would enable management to assess the relative alarm remediation performance of a given region, district, office, area, etc. The alarm age module 70 may include an internal database application operable for storing and archiving pressurization-related data and summary information, and may display those data and information via a spreadsheet application and a graphical user interface (GUI). The alarm age module 70 may also be in communication with a printer 72 operable for printing the summary information generated by the alarm age module 70. The alarm age module 70 may also be in communication with an external database application 74 operable for storing and archiving the data and summary information.

Figure 2:
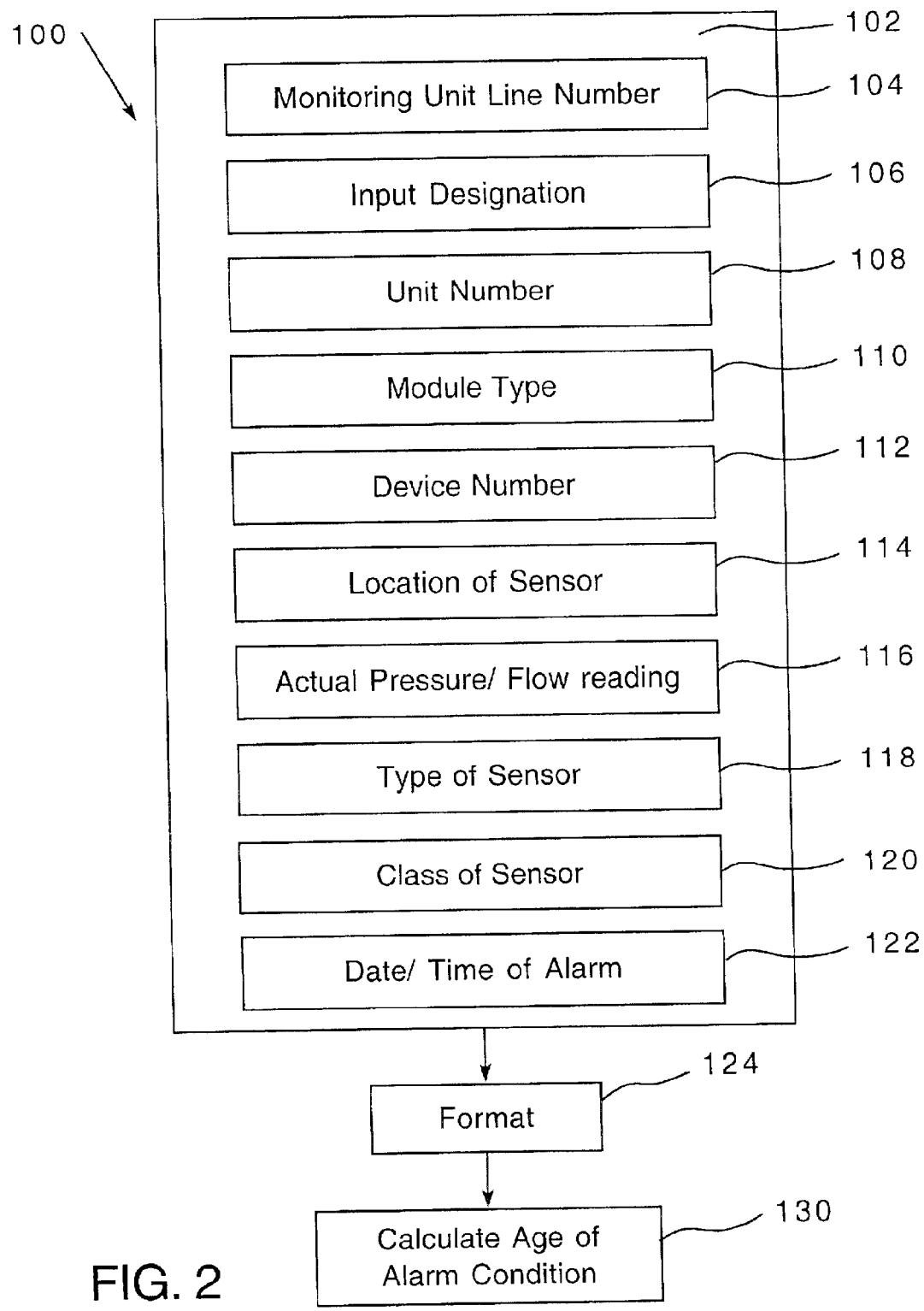
FIG. 2 is a partial flow chart of on embodiment of a method for tracking the age of an alarm condition within a pressurized cable network.
Figure 2A:
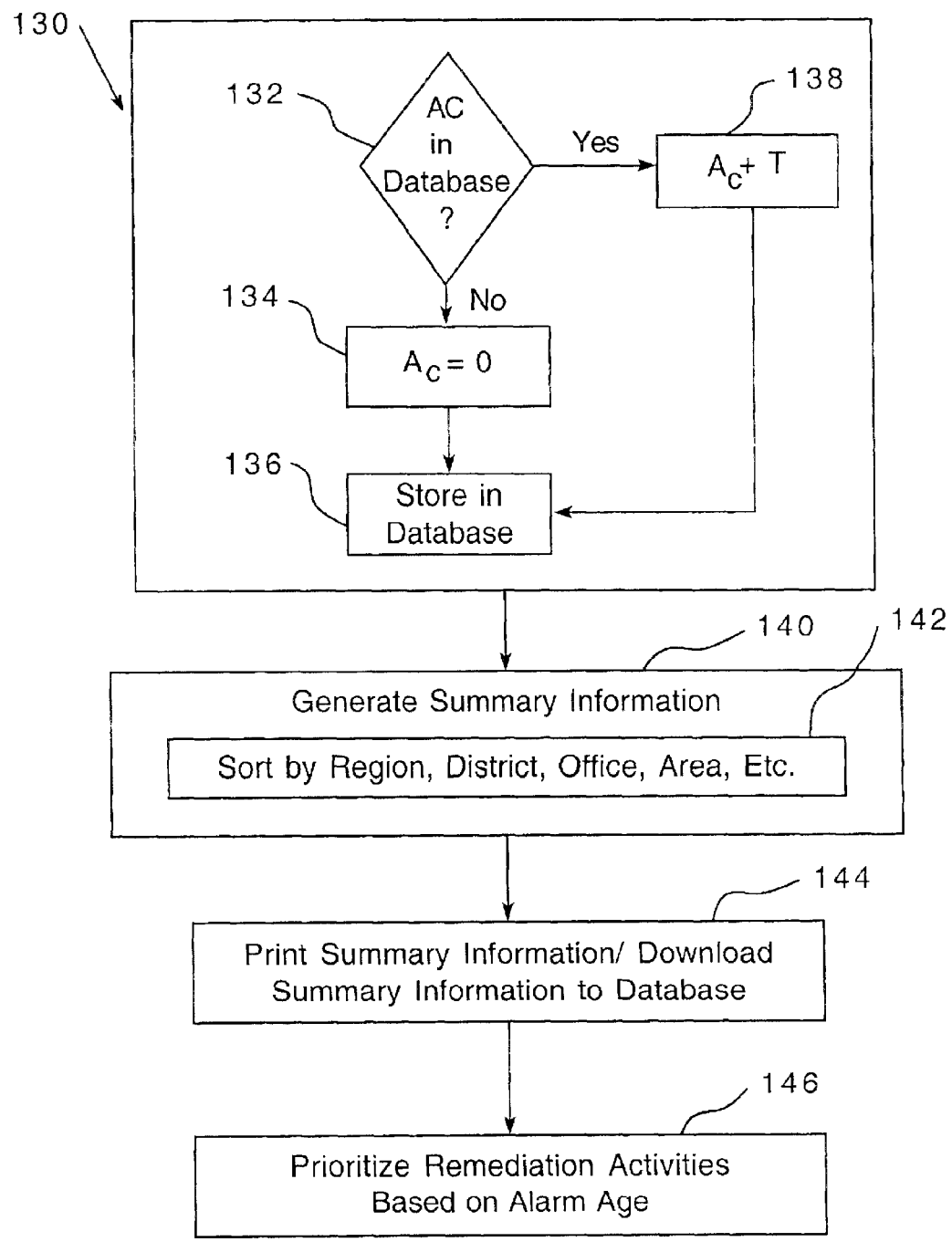
FIG. 2A is another partial flow chart of the method embodiment depicted in FIG. 2.

One embodiment of the present invention also includes a method 100 for managing the flow and pressure of a fluid within a network of pressurized cable-carrying conduits, such as a pressurized telecommunications cable network 12. As can be seen in FIGS. 2 and 2A, the method 100 may include collecting alarm-related data from various central offices 40 (FIG. 1) via a computer network 50 (FIG. 1), such as a LAN, a WAN, or the Internet (block 102). Such data collection may occur in accordance with a predetermined time schedule. For example, the data may be collected on an hourly, daily, weekly, monthly, etc. time basis. These data may be categorized by wire center 20 and include information relating to the particular sensor (28, 30) that tripped the alarm 44, the monitoring unit line number (block 104) wherein information relating to that sensor can be found, the input designation (block 106) for the sensor which is the dedicated pressure, the unit number (block 108) which is the particular route number, and the type of module (block 110) which may be a subscriber, dedicated or addressable module. Still other data that may be collected include the device number (block 112) that is a unique device identifier, and the actual geographic location of the sensor (block 114). Additional collected data may include the actual pressure/flow reading (block 116) for the sensor that tripped the alarm, and the type of sensor (block 118) involved. For example, there may be pressure transducers, flow transducers, humidity sensors, moisture contact sensors, etc. The collected data may also identify the sensor's class (block 120) which may be for example, an air pipe class, and underground class, buried class, aerial class, etc. Examples of such class designators are: "PP" (pressure pipe), "UP" (underground pressure), "BP" (buried pressure), "AP" (aerial pressure), etc. The data may also include the date and time that an alarm was received (block 122). This data may be formatted (block 124) or sorted and stored or archived by wire center, central office, manager, etc. In addition, after an alarm condition has been remedied, the information may be archived for use in other system maintenance applications.

After the data have been collected and, if desired, formatted, the age of each alarm condition (block 130) is determined by the alarm age module 70. The time period (i.e., hours, days, weeks, months, etc.) in which the alarm age is determined may coincide with the time period in which the data is periodically collected. For example, if the data are collected on a daily basis, the age of the alarm condition may be set forth in days. Those of ordinary skill in the art will appreciate, however, that other programs could be used to convert such age value into other periods of time, such as seconds, hours, weeks, months, etc.

Turning to FIG. 2A, when alarm data are received by the alarm age module 70, the module 70 determines whether it has data therein relating to the current age (Ac) of the alarm condition or whether this is the initial receipt of such information (block 132). If the module 70 has no prior information about the alarm age (Ac) in its internal database, the module 70 assigns a value of zero time periods to Ac (block 134). That information is then stored within the internal database within module 130 (block 136) and may also be summarized (block 140) and, if desired, sorted by region, district, office, area, etc. (block 142) and then printed/downloaded to database 74 (block 144). If the module 70 has current age information for that particular alarm in its internal data base, module 70 updates the current age (Ac) by adding the number of time periods (T) that have passed since the current age (Ac) was previously established or updated (block 138). The updated alarm age is then stored in the internal database (block 136) and may also be summarized (block 140), sorted (block 142), printed/ downloaded to database 74 (block 144). It will be appreciated that, if management finds it more desirable to calculate the alarm age value in other time periods, the alarm age module may contain a conversion application to do so. Management may then be able to use this information to prioritize remediation activities based on alarm age to ensure that the oldest alarm conditions are receiving appropriate priority attention (block 146).

An exemplary report 160 generated using at least one embodiment of the systems and methods of the present invention is set forth in FIG. 3. The report 160 identifies each alarm condition by wire center 162, line number 164 (Line), input number 166 (Input), unit number 168 (Unit), module number 170 (Mod), device number 172 (Dev #), type and location of the sensor 174 (CO Panel Alarms Min PSI 9.5/Max PSI 11.0), the actual pressure reading 176 (Read), the type of device 178 (Dev Type), the class of device 180 (Class), the date of the report 182 (Date), the time that the alarm was first generated 184 (Time), the date on which the alarm first occurred 186 (Alm-Date) and the alarm age in time periods (hours, days, weeks, months, etc.) 188 (Alm Age). Such reports will enable a management to monitor the remediation progress and prioritization of alarm conditions occurring within networks of pressurized cables.

Thus, from the foregoing discussion, it is apparent that various embodiments of the present invention provide the user with methods for monitoring the age of alarm conditions occurring within a pressurized cable network. While the present invention has been shown and described in conjunction with examples and preferred embodiments thereof, variations in and modifications to the present invention may be effected by persons of ordinary skill in the art without departing from the sprit and scope of the present invention. It is therefore to be understood that the principles described herein may apply in a similar manner, where applicable, to all examples and preferred embodiments and the following claims are intended to cover all equivalents embodiments.

What is claimed is:

1. A method of monitoring pressurization performance of a network of pressurized telecommunications cables, comprising:

detecting pressure alarm conditions within the network;

recording the time and date during which each pressure alarm condition was initially detected; and calculating a length of time for each detected pressure alarm condition during which the detected pressure alarm condition remains unremediated.

2. The method of claim 1 wherein the calculating is done periodically.

3. The method of claim 2 wherein the calculating is done daily.

4. The method of claim 1 wherein the detecting comprises:

monitoring a pressure of a fluid within the network;

comparing the monitored pressure to a predetermined range of pressures; and identifying an alarm condition for each time the monitored pressure is less than a predetermined minimum pressure.

5. The method of claim 4 wherein the monitoring a pressure of a pressurized fluid comprises monitoring a plurality of pressure sensors within the network.

6. The method of claim 5 wherein the plurality of pressure sensors are operable for monitoring air pressure.

7. The method of claim 1 wherein the detecting comprises:

monitoring a flow rate of a pressurized fluid within the network;

comparing the monitored flow rate to a predetermined range of flow rates; and identifying an alarm condition for each time the monitored flow rate falls outside of the predetermined range of flow rates.

8. The method of claim 7 wherein the monitoring a flow rate comprises monitoring a plurality of air flow sensors within the network.

9. The method of claim 7 further comprising generating a report containing an age for each unremediated pressure alarm and for each unremediated flow rate alarm as of a report generation date.

10. The method of claim 1 wherein the detecting comprises:

monitoring a pressure of a pressurized fluid within the network;

comparing the monitored pressure to a predetermined range of pressures;

identifying an alarm condition for each time the monitored pressure is less than a predetermined minimum pressure;

monitoring a flow rate of the pressurized fluid within the network;

comparing the monitored flow rate to a predetermined range of flow rates;

identifying another alarm condition for each time the monitored flow rate falls outside of the predetermined range of flow rates.

11. The method of claim 1 further comprising generating a report containing an age for each unremediated alarm condition as of a report generation date.

12. A method for monitoring the remediation of leaks within a network of pressurized telecommunications cables, comprising:

monitoring a pressure of a fluid within the network;

comparing the monitored pressure to a predetermined minimum pressure;

initiating a pressure alarm when the monitored pressure is less than the predetermined minimum pressure; and calculating a length of time during which the monitored pressure remains less than the predetermined minimum pressure.

13. The method of claim 12 wherein the monitoring a pressure of a fluid comprises monitoring a plurality of pressure sensors within the network.

14. The method of claim 13 wherein the plurality of pressure sensors are operable for monitoring air pressure.

15. The method of claim 12 further comprising generating a report containing an age for each unremediated pressure alarm as of a report generation date.

16. The method of claim 12 further comprising:

monitoring a flow rate of the fluid within the network;

comparing the monitored flow rate to a predetermined minimum flow rate;

initiating a flow rate alarm when the monitored flow rate is less than the predetermined minimum flow rate; and monitoring a length of time during which the flow rate alarm remains unremediated.

17. The method of claim 16 wherein said monitoring a flow rate comprises monitoring a plurality of air flow sensors within the network.

18. A method for monitoring the remediation of leaks within a network of pressurized cable-carrying conduits, comprising:

monitoring a pressure of a fluid within the network of pressurized cable-carrying conduits;

comparing the monitored pressure to a predetermined maximum pressure;

initiating a pressure alarm when the monitored pressure is greater than the predetermined maximum pressure; and calculating a length of time during which the pressure alarm remains unremediated.

19. The method of claim 18 wherein said monitoring a pressure of a fluid comprises monitoring a plurality of pressure sensors within said pressurized cable-carrying conduits.

20. The method of claim 19 wherein said plurality of pressure sensors are operable for monitoring air pressure.

21. The method of claim 18 further comprising generating a report containing an age for each unremediated pressure alarm as of a report generation date.

22. The method of claim 18 further comprising:

monitoring a flow rate of the fluid within the network of pressurized cable-carrying conduits;

comparing the monitored flow rate to a predetermined maximum flow rate;

initiating a flow rate alarm when the monitored flow rate is greater than the predetermined maximum flow rate; and monitoring a length of time during which the flow rate alarm remains unremediated.

23. The method of claim 22 wherein said monitoring a flow rate comprises monitoring a plurality of air flow sensors with the pressurized cable carrying conduits.

24. A method for monitoring the pressurization performance of a network of pressurized cable-carrying conduits, comprising:

monitoring a pressure of a fluid within the network of pressurized cable-carrying conduits;

comparing the monitored pressure to a predetermined minimum pressure and a predetermined maximum pressure;

initiating a pressure alarm when the monitored pressure is less than the predetermined minimum pressure or greater than the predetermined maximum pressure; and monitoring a length of time during which the pressure alarm remains unremediated.

25. The method of claim 24 wherein said monitoring a pressure of a fluid comprises monitoring a plurality of pressure sensors within said pressurized cable-carrying conduits.

26. The method of claim 25 wherein said plurality of pressure sensors are operable for monitoring air pressure.

27. The method of claim 24 further comprising generating a report containing an age of the unremediated pressure alarms.

28. The method of claim 24 further comprising:

monitoring a flow rate of the fluid within the network of pressurized cable-carrying conduits;

comparing the monitored flow rate to a predetermined minimum flow rate and a maximum flow rate;

initiating a flow rate alarm when the monitored flow rate is less than the predetermined minimum flow rate and greater than the predetermined maximum flow rate; and monitoring a length of time during which the flow rate alarm remains unremediated.

29. The method of claim 28 further comprising generating a report containing an age of the unremediated pressure alarms and an age of the unremediated flow rate alarms.

30. A telecommunications cable system comprising:

a network of pressurized telecommunications cables;

at least one source of compressed fluid coupled to the network;

at least one pressure sensor coupled to the network;

at least one monitoring unit for monitoring pressures sensed by the pressure sensors and comparing said monitored pressures to a predetermined range of pressures;

at least one alarm triggered by the monitoring unit each time one of the monitored pressures falls outside of the predetermined range of pressures;

a computer network communicating with the monitoring unit for receiving data about the triggered alarms; and an alarm age module operable for receiving the data about each triggered alarm from the computer network and determining a length of time for each of the triggered alarms during which the triggered alarm remained unremediated.

31. The system of claim 30 wherein the alarm age module is operable to prepare a report containing ages of unremediated triggered alarms.

32. The system of claim 30 wherein the source of compressed fluid comprise at least one air compressor located in at least one wire center.

33. The system of claim 32 wherein the monitoring units are located in a central office and communicate with the pressure sensors in a portion of the network.

34. The system of claim 33 wherein the alarm age module is operable to prepare a report containing ages of unremediated triggered alarms for each of the wire centers.

35. The system of claim 34 wherein the data about the triggered alarm comprises data selected from the group consisting of: a line number corresponding to the triggered alarm, an input designation corresponding to the triggered alarm, a unit designation corresponding to the triggered alarm, a module designation corresponding to the triggered alarm, a device number corresponding to the triggered alarm, a location of the pressure which resulted in the triggered alarm, a pressure reading of the sensor which resulted in the triggered alarm, a device type for the triggered alarm, a class type of the triggered alarm, a date on which the report was generated, a time that the alarm was triggered, and a date on which the alarm was triggered.

36. A telecommunications cable system comprising:

a network of pressurized telecommunications cables;

at least one source of compressed fluid coupled to the network;

at least one pressure sensor coupled to the network;

at least one flow sensor coupled to the network for sensing flow rates of said compressed fluid within the network;

at least one monitoring unit for monitoring pressures detected by the pressure sensors and comparing the monitored pressures to a predetermined range of pressures, the monitoring unit monitoring flow rates sensed by the flow rate sensors and comparing the monitored flow rates to a predetermined range of flow rates;

at least one alarm triggered by the monitoring unit each time one of the monitored pressures falls outside of the predetermined range of pressures and each time one of the monitored flow rates falls outside of the predetermined range of flow rates;

a computer network communicating with the monitoring unit for receiving data about the triggered alarm; and an alarm age module operable for receiving said data about each of the triggered alarms from the computer network and determining a length of time for each of the triggered alarms during which the triggered alarm remained unremediated.

37. The system of claim 36 wherein the alarm age module is operable to prepare a report containing ages of unremediated triggered alarms.

38. The system of claim 36 wherein the source of compressed fluid comprises at least one air compressor located in at least one wire center.

39. The system of claim 38 wherein the monitoring units are located in a central office and communicate with the pressure sensors in a portion of the network.

40. The system of claim 39 wherein the alarm age module is operable to prepare a report containing ages of unremediated triggered alarms for each said wire center.

41. The system of claim 40 wherein the data about the triggered alarm comprises data selected from the group consisting of: a line number corresponding to the triggered alarm, an input designation corresponding to the triggered alarm, a unit designation corresponding to the triggered alarm, a module designation corresponding to the triggered alarm, a device number corresponding to the triggered alarm, a location of the pressure which resulted in the triggered alarm, a pressure reading of the sensor which resulted in the triggered alarm, a device type designation for the triggered alarm, a class type designation of the triggered alarm, a date on which the report was generated, a time that the alarm was triggered, and a date on which the alarm was triggered.

42. A computer-readable medium having executable commands operable for monitoring the age of an unremediated alarm condition in a network of pressurized cable network, comprising:

monitoring at least one pressure sensor in the pressurized cable network;

triggering a pressure alarm when a pressure detected by one of the pressure sensors falls outside of a predetermined range of pressures;

receiving data related to the pressure sensors that detected the pressure falling outside of the predetermined range of pressures; and calculating a number of time periods during which the detected pressure remained outside of the predetermined range of pressures.

43. The computer readable medium of claim 42 wherein the time periods are selected from the group consisting of seconds, hours, days, weeks, months, and years.

44. A computer system comprising:

a computer for receiving data about triggered pressure alarms; and a pressure alarm age module within the computer for determining a length of time for each of the triggered pressure alarms during which the triggered pressure alarms remained unremediated, said pressure alarm age module being operable to prepare a report containing ages of unremediated triggered pressure alarms.

45. The computer system of claim 44 wherein the triggered pressure alarms comprise fluid pressure alarms.

46. The computer system of claim 44 wherein the triggered pressure alarms comprise fluid flow alarms.

* * * * *